(12) United States Patent
Håkansson

(10) Patent No.: US 10,416,105 B2
(45) Date of Patent: Sep. 17, 2019

(54) DIBASIC ACID SENSOR AND METHOD FOR CONTINUOUSLY MEASURING DIBASIC ACID CONCENTRATION IN A SUBSTANCE

(71) Applicant: ALSTOM Technology Ltd., Baden (CH)

(72) Inventor: Rikard Håkansson, Växjö (SE)

( * ) Notice: Subject to any disclaimer, the term of this patent is extended or adjusted under 35 U.S.C. 154(b) by 0 days.

(21) Appl. No.: 15/177,412

(22) Filed: Jun. 9, 2016

(65) Prior Publication Data

US 2017/0023507 A1    Jan. 26, 2017

(30) Foreign Application Priority Data

Jun. 12, 2015   (EP) .................................... 15171963

(51) Int. Cl.
*G01N 27/06* (2006.01)
*B01D 53/34* (2006.01)
(Continued)

(52) U.S. Cl.
CPC ............ *G01N 27/06* (2013.01); *B01D 53/346* (2013.01); *B01D 53/504* (2013.01); *G01N 27/48* (2013.01);
(Continued)

(58) Field of Classification Search
CPC ........ G01N 27/00; G01N 27/02; G01N 27/04; G01N 27/06; G01N 27/48; G01N 17/00;
(Continued)

(56) References Cited

U.S. PATENT DOCUMENTS 1,659,832 A    2/1928  Nelson
4,336,035 A    6/1982  Evenstad
(Continued)

FOREIGN PATENT DOCUMENTS

CN    85204611    7/1986
CN    201320718   10/2009
(Continued)

OTHER PUBLICATIONS

Lee Y J et al, "Oxidative degradation of organic acid conjugated with sulfite oxidation in flue gas desulfurization: Products, kinetics, and mechanism", Environmental Science & Technology,1987, pp. 266-272, vol. 21—No. 3.

(Continued)

*Primary Examiner* — Hoai-An D Nguyen
(74) *Attorney, Agent, or Firm* — GE Global Patent Operation; Rita D. Vacca

(57) ABSTRACT

A method for measuring a concentration of dibasic acid in a cleaning process substance is provided. The method includes sending a plurality of voltage pulses through the cleaning process substance by each a first electrode and a second electrode. Each the first electrode and the second electrode is in contact with the cleaning process substance containing a concentration of dibasic acid. The method also includes receiving current responses generated by the plurality of voltage pulses, and analyzing the current responses using a multivariate data analysis for calculation of the concentration of dibasic acid in the cleaning process substance. A dibasic acid sensor, a control unit, and an analyzing unit for performing the method, are also provided.

19 Claims, 5 Drawing Sheets

(51) Int. Cl.
*B01D 53/50* (2006.01)
*G01N 27/48* (2006.01)

(52) U.S. Cl.
CPC .. *B01D 2252/205* (2013.01); *B01D 2257/302* (2013.01)

(58) Field of Classification Search
CPC ...... G01N 17/006; G01N 17/02; G01R 27/00; B01D 53/346; B01D 53/504; B01D 2252/205; B01D 2257/302
USPC ................................ 324/600, 649, 691, 693
See application file for complete search history.

(56) References Cited

U.S. PATENT DOCUMENTS

| | | | |
|---|---|---|---|
| 4,336,102 | A | 6/1982 | Jacobs et al. |
| 4,502,872 | A | 3/1985 | Ivester |
| 5,569,436 | A * | 10/1996 | Lerner .................. B01D 53/64 110/235 |
| 6,403,256 | B1 | 6/2002 | Gan et al. |
| 7,625,537 | B2 * | 12/2009 | Rader .................... B01D 53/10 422/168 |
| 9,440,183 | B2 * | 9/2016 | Brogaard ............. B01D 53/346 |
| 9,468,885 | B2 * | 10/2016 | Laslo .................... B01D 47/06 |
| 2011/0206813 | A1 | 8/2011 | Shen et al. |
| 2014/0231272 | A1 * | 8/2014 | Brogaard ........... G01N 27/4162 205/782 |

FOREIGN PATENT DOCUMENTS

| | | |
|---|---|---|
| CN | 102128862 | 7/2011 |
| EP | 0162536 | 11/1985 |
| EP | 1219957 A1 | 7/2002 |
| EP | 1010005 | 7/2008 |
| EP | 2110660 | 4/2009 |
| EP | 2578292 A1 | 4/2013 |
| EP | 2579032 A1 | 4/2013 |
| JP | 0275322 | 3/1990 |
| JP | 05317643 | 12/1993 |
| JP | 06182148 | 7/1994 |
| JP | 11104448 | 4/1999 |
| JP | 2948330 B2 | 9/1999 |
| SU | 1659832 | 6/1991 |
| TW | 524717 B | 3/2003 |
| WO | 9913325 | 9/1998 |
| WO | 0244460 | 6/2002 |
| WO | 02052254 | 7/2002 |
| WO | 03046554 | 6/2003 |
| WO | 2004053476 | 6/2004 |

OTHER PUBLICATIONS

Wold, S et al, "Principal component analysis: A tutorial", Chemometrics and Intelligent Laboratory Systems 2, 1987, 37-52.
S. Wold et al., "PLS-regression: a basic tool of chemometrics", Chemometrics and ntelligent Laboratory Systems, 2001, 109-130, 58.
European Search Report issued in connection with corresponding EP Application No. 15171963.0 dated Dec. 3, 2015.
Winquist et al., "Electronic Tongues", MRS Bulletin, pp. 1-6, vol. No. 29, Issue No. 10, Oct. 2004.
Unofficial English Translation of Chinese Office Action issued in connection with corresponding CN Application No. 201280053533.5 dated Mar. 31, 2015.
Woodis et al—"Volumetric method for control of ammonia scrubbing process for removal of sulfur dioxide form stack gases"—Environmental Science & Technology, vol. 7, No. 9, Sep. 1, 1973.
Garber et al—"Determination of atmospheric sulfur dioxide by differential pulse polarography"—Analytical Chemistry, vol. 44, No. 8, Jul. 1, 1972.
Labrador et al—"Determination of Bisulfites in Wines with an Electronic Tongue Based on Pulse Voltammetry"—Electroanalysis 2009, 21, No. 3-5, 612-617.
European Search Report corresponding to EP Appln. No. 11184432.0, dated Mar. 7, 2012.
The International Search Report and the Written Opinion of the International Searching Authority corresponding to PCT Appln. No. PCT/IB2012/055433 dated Jan. 16, 2013.
Skavas et al., "Kinetics and mechanism of sulphite oxidation on a rotating platinum disc electrode in an alkaline solution", ScienceDirect May 8, 2006.
Hemmingsen et al., "The Electrochemical Reaction of Sulphur-oxygen Compounds-part II. Voltammetric Investigation performed on Platinum" Electrochimica Acta vol. 37 No. 15, Jan. 1992.
Winquist et al., "An electronic tongue based on voltammetry" Elsevier Jun. 28, 1997.
Heering et. al., "Using the Pulsed Nature of Staircase Cyclic Voltammetry to Determine Interfacial Electron-Transfer Rates of Adsorbed Species" , Dept. of Chemistry Oxford University 1999.
Adeloju et. al: " Polypyrrole-Based Amperometric Biosensor for Sulfite Determination" Electroanalysis, 6(1994) 865-870.
Bott: "A Comparison of Cyclic Voltammetry and Cyclic Staircase Voltammetry", Current Separtions 16:1, 1997.

* cited by examiner

DIBASIC ACID SENSOR AND METHOD FOR CONTINUOUSLY MEASURING DIBASIC ACID CONCENTRATION IN A SUBSTANCE

TECHNICAL FIELD

The present disclosure relates to a dibasic acid sensor operative for continuously measuring the concentration of dibasic acid in a substance used in a gas cleaning device.

The present disclosure further relates to a method for continuously measuring a concentration of dibasic acid in a substance used in a gas cleaning device.

BACKGROUND

Process gases containing acid gases are generated in many industrial processes. Such an industrial process may be the combustion of a fuel such as coal, oil, peat, waste, or similar combustible, in a combustion plant such as a power plant, whereby a hot process gas or "flue gas" is generated containing pollutants including acid gases. The generated process gas requires treatment for removal of at least a portion of the acid gases present therein prior to release of the process gas into the atmosphere. Such process gas treatment may be provided in a wet scrubber such as that disclosed in EP 0 162 536. The disclosed wet scrubber comprises an absorption liquid, which is brought into contact with the process gas for absorption of at least a portion of the acid gases from the process gas. The absorption liquid brought into contact with the process gas may be atomized through nozzles to react with the process gas.

Dibasic acid (DBA) is an aliphatic dibasic acid product containing primarily glutaric, succinic and adipic acids available commercially from companies such as INVISTA, a wholly owned subsidiary of Koch Industries, Inc., Wichita, Kans., USA and Sigma-Aldrich Corporation, St. Louis, Mo., USA. DBA is a substance used within wet flue gas desulphurization (WFGD) systems to improve sulphur dioxide removal efficiency. DBA acts as a buffer in WFGD systems to boost the absorption liquid's availability to absorb sulphur dioxide, to thereby remove sulphur dioxide from the process gas, with reduced pH level drop of the absorption liquid. Hence, DBA increases the alkalinity of the absorption liquid without changing the pH of the absorption liquid.

Because DBA use increases the efficiency of sulphur dioxide removal from process gas, DBA use is very desirable. Unfortunately, use of DBA in WFGD systems is relatively expensive. Further, overages or overdosing of DBA in the absorption liquid may lead to waste water treatment difficulties and additional expenses associated therewith. Accordingly, in order to minimize WFGD system operating expenses and avoid waste water treatment difficulties and expenses associated therewith, DBA concentration maintenance to a level sufficient to achieve a desired WFGD system efficiency without overdosing thereof, is desirable.

Consequently, there is a need for continuously measuring DBA concentration in a substance in a gas cleaning device for process gas cleaning treatment process control.

BRIEF DESCRIPTION

Embodiments of the invention relate to a dibasic acid (DBA) sensor operative for continuously measuring the concentration of DBA present in a substance used in a gas cleaning device, and a method for continuously measuring a concentration of DBA present in a substance used in a gas cleaning device.

In an embodiment, a method of measuring a concentration of DBA present in a substance used in a gas cleaning process includes sending a plurality of voltage pulses through the substance by a first electrode and a second electrode, which first and second electrodes are in contact with the substance, receiving current responses generated by the plurality of voltage pulses, and analyzing the current responses generated using multivariate data analysis to calculate the concentration of DBA present in the substance to obtain a calculated DBA concentration.

BRIEF DESCRIPTION OF THE DRAWINGS

The present disclosure is described in more detail with reference to the drawings, in which.

DETAILED DESCRIPTION

Figure 1:
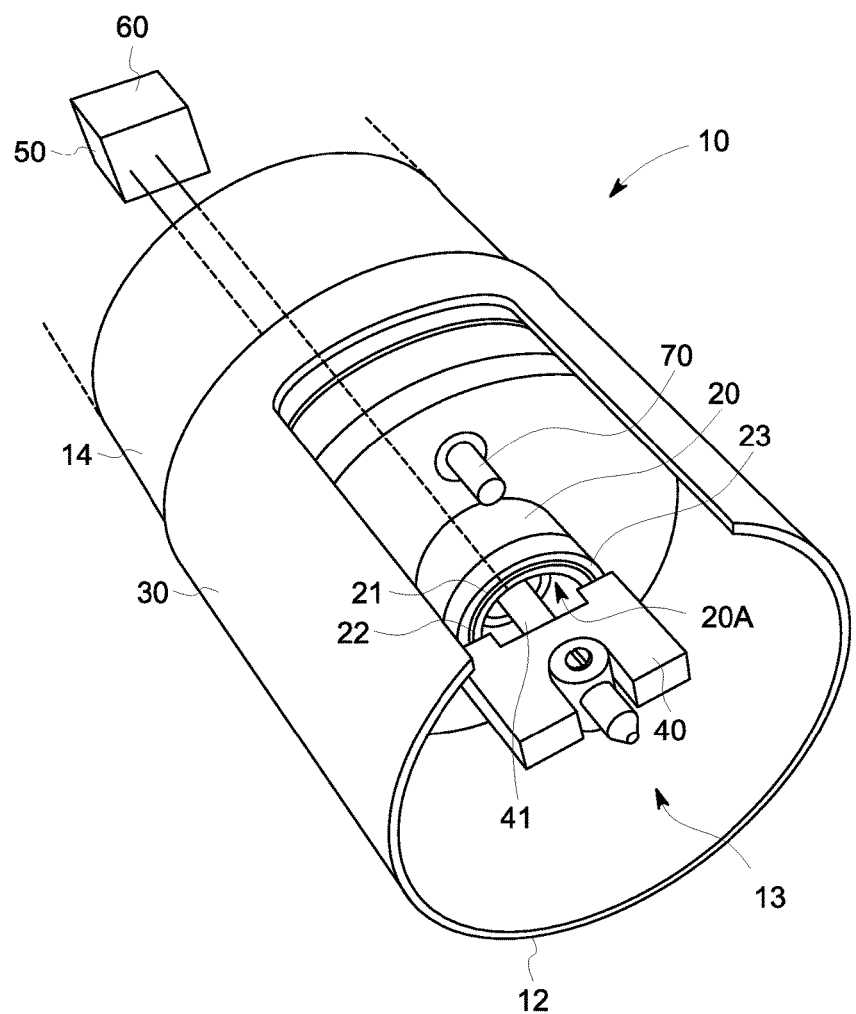
FIG. 1 is a perspective view of a dibasic acid sensor according to an embodiment.

The present disclosure is described more fully hereinafter with reference to the accompanying drawings, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. In the drawings, like numbers refer to like elements.

Embodiments of the invention relate to methods for measuring a concentration of DBA present in a substance used in a gas cleaning process. In one aspect, for example, a method comprises sending a plurality of voltage pulses through the substance by a first electrode and a second electrode (the first and second electrodes are in contact with the substance), receiving current responses generated by the plurality of voltage pulses, and analyzing the current responses generated using multivariate data analysis to calculate the concentration of DBA present in the substance to obtain a calculated DBA concentration.

In an embodiment of this method, the DBA concentration within the substance may be continuously "measured." Further, by the present method, even a relatively low concentration of DBA may be continuously measured with relatively high accuracy. Also, continuously measuring the DBA concentration present within the substance allows for DBA concentration control with relatively high accuracy. For example, if the substance is an absorption liquid contained within a wet scrubber of a wet flue gas desulfurization (WFGD) system that uses limestone as the absorbent liquid, the subject method provides for continuous measurement of DBA concentration present in the absorption liquid to thereby control the concentration of DBA present within the absorbent liquid for increased wet scrubber $SO_2$ removal efficiency without DBA overdosing. For this purpose, the subject method uses a voltammetric method for measuring the DBA concentration present in the absorption liquid. This voltammetric method uses voltage pulses sent over a first and a second electrode of a DBA sensor arranged in the absorption liquid. The second electrode may be a large piece of metal. The second electrode may have an area, which is at least 20 times larger than that of the first electrode. The current responses generated by the voltage pulses are then analyzed using multivariate data analysis, and mathematical models from samples with known dibasic acid concentrations to create a prediction model useful for determining the dibasic acid concentration present in the absorption liquid for control thereof. The subject disclosure focuses on continuously measuring DBA concentraion present in a substance. However, other components present in a substance, such as in a limestone absorption liquid contained within a wet scrubber of a WFGD system, may be continuously measured and controlled such as described herein for DBA. For example, as disclosed herein for DBA, sulfides such as $S^{2-}$ used for mercury control may be continuously measured using a sulfide sensor that measures sulfide concentration present in the absorption liquid to thereby control the concentration of sulfides present within the absorption liquid to achieve desired mercury removal efficiency. Depending on the concentration of sulfides present within the absorption liquid, the dosing rate of a sulfide additive to the absorption liquid is controlled to achieve the desired sulfide concentration and hence mercury removal efficiency.

As another example, as disclosed herein for DBA, sulfites such as $SO_3^{2-}$ may be continuously measured using a sulfite sensor that measures sulfite concentration present in the absorption liquid to thereby control the concentration of sulfites present within the absorption liquid. Depending on the concentration of sulfites present within the absorption liquid, oxygenation of the absorption liquid is increased, maintained or decreased. Further, other components present in a substance, such as in a limestone absorption liquid contained within a wet scrubber of a WFGD system, may be continuously measured and controlled such as described herein for DBA. For example, as disclosed herein for DBA, chlorides, $Cl^-$, bromides, $Br^-$, magnesium, $Mg^{2+}$, sodium, $Na^+$, nitrates, $NO_3^{2-}$, and nitrites, $NO_2^{2-}$, may be continuously measured using a chloride sensor, a bromide sensor, a magnesium sensor, a sodium sensor, a nitrate sensor and a nitrite sensor, respectively, that measures the chloride, bromide, magnesium, sodium, nitrate, and nitrite concentrations, respectively, present in the absorption liquid to thereby control the concentration thereof present within the absorption liquid to enable control thereof. Hence, depending on the concentration of chloride, bromide, magnesium, sodium, nitrate and/or nitrite present within the absorption liquid, an absorption liquid release or bleed from the wet scrubber may be increased, maintained or decreased to achieve the desired concentrations thereof to control process efficiency.

Still further, DBA and other components present in a substance, such as a limestone absorption liquid contained within a wet scrubber of a WFGD system, may be continuously measured and controlled such as described herein for DBA, using a single sensor. As such, the single sensor is programmed as described above for continuously measuring the concentration of a first component present in the absorption liquid, and also programed as described above for continuously measuring the concentrations of one or more additional components present in the absorption liquid for control thereof. For example, as disclosed above for continuously measuring the concentration of DBA, a single sensor using a voltammetric method sends pulses over a first and a second electrode of a multicomponent sensor arranged in the substance to measure the concentration of a first component present in the substance. The second electrode may be a large piece of metal. The second electrode may have an area, which is at least 20 times larger than that of the first electrode. The current responses generated by the voltage pulses are then analyzed using multivariate data analysis, and mathematical models from samples with known first component concentrations to create a prediction model useful for determining the first component concentration present in the substance for control thereof. Then the same multicomponent sensor using a voltammetric method sends pulses over the first and the second electrode arranged in the substance to measure the concentration of a second component present in the substance. The current responses generated by the voltage pulses are then analyzed using multivariate data analysis, and mathematical models from samples with known second component concentrations to create a prediction model useful for determining the second component concentration present in the substance for control thereof. Once the multicomponent sensor is so programmed, the single multicomponent sensor may be used to continuously measure the concentrations of two or more components selected from the group consisting of DBA, sulfides, sulfites, chlorides, bromides, magnesium, sodium, nitrates, and nitrites, present in the substance to enable control thereof. Although a single sensor may be programmed and used as disclosed herein to continuously measure the concentration of one or more components present in a substance, for purposes of clarity and simplicity, only a DBA sensor used to continuously measure the concentration of DBA present in the substance for control thereof will be discussed in detail herein, although the disclosure is equally applicable to these further embodiments as just described.

According to one embodiment of the subject disclosure, the step of sending a plurality of voltage pulses may comprise sending the plurality of voltage pulses in a series, stepwise increasing and/or decreasing the voltage level.

By increasing and/or decreasing the voltage level stepwise, a series of voltages sent through the first electrode may result in data generation in the shape of a staircase. As an alternative depending on component, by alternating the voltage, a series of voltages sent through the first electrode may result in data generation. As another alternative depending on component, by using an average constant voltage, a series of voltages sent through the first electrode may result in data generation. In the case of increasing and/or decreasing the voltage level stepwise, a voltage pulse generating a current response may occur when the voltage level is increased or decreased to a new level. During DBA concentration measurement, the voltage levels may be swept in steps from a first voltage level to a final voltage level. The first voltage level may be a negative voltage and the final voltage level a positive voltage, resulting in an anodic sweep. Alternatively, the first voltage level may be a positive voltage and the final voltage level may be a negative voltage, resulting in a cathodic sweep.

According to one embodiment, analyzing the current responses generated comprises analyzing peaks of the current responses using multivariate data analysis. This embodiment may be beneficial in that multivariate data analysis efficiently provides continuous DBA concentration measurement using the current responses generated.

According to one embodiment, analyzing current responses comprises analyzing a peak value and at least one more value for each current response generated using multivariate data analysis.

According to one embodiment, continuously measuring DBA concentration present in a substance, a series of voltages are sent through a first electrode, generating as a result, a series of current responses. The peak shape of each current response generated may provide feedback information regarding the DBA concentration present in the substance. The current response generated may include a peak level and a decay of the current. Each current response generated may be sampled in a number of samples providing a number of values. Analyzing the peak value and at least one more value of each current response generated may provide enough feedback information for using the multivariate data analysis to estimate the DBA concentration present in the substance. The amount of data used in the analysis is thereby reduced as compared to analyzing a complete peak or a large number of data values, e.g., all sample values. Using only the two values may still provide reliable continuous measurement of the DBA concentration present in the substance. DBA may have a redox potential at which a current response may be increased compared to other potentials. When a series of voltage pulses approach a voltage level corresponding to the redox potential of DBA, the current response may provide a peak shaped increased current level. Such increased current level may be identified when analyzing the peak value of each current response generated. In one embodiment, the at least one value besides the peak value may be four values. Such values may be taken at the decay of the current response to provide further information regarding the DBA concentration present in the substance. As an example, each current response may be sampled in 50 samples. If five values, including the peak value, may be analyzed using multivariate data analysis, three of the values, including the peak value, may be taken from the first third of the samples. Further, one value may be taken from a second third of the samples, and one value may be taken from a last third of the samples. In one embodiment, the peak value may be from the first or second sample of each current response.

According to one embodiment, the method may further comprise cleaning a surface of the first electrode from a coating caused by contact between the first electrode and the substance.

The first electrode may be made of platinum, gold, iridium, silver or similar metal material, but in embodiments, it is made of platinum. When measuring in a substance containing compounds, such as sulphurous compounds, the first electrode may rather quickly become unusable due to binding on the platinum surface of the electrode. This may form a coating on the electrode surface and negatively affect measurement results. By cleaning the surface of the electrode, the coating may be removed to ensure measurement reliability. The cleaning of the electrode may be made continuously, or semi-continuously. The cleaning may be performed by a cleaning unit, such as a brush, a grinder, a scraper or the like.

According to one embodiment the amount of each voltage pulse sent through the substance may be approximately 0.02 to approximately 1.0 V higher or lower than an immediately preceding voltage pulse.

Each voltage pulse may be an increase or a decrease in the voltage level. The voltage level may be increased or decreased at an amount of approximately 0.02 to approximately 1.0 V for each voltage pulse. More particularly, the voltage level may be increased or decreased in an amount of about 0.5 V. A complete measurement of DBA concentration present in the substance may for instance start with a voltage of approximately −0.9 V, which is in a stepwise manner increased up to approximately 0.8 V. A current response may be received for each voltage pulse or step. After a voltage sweep, a plurality of current responses generated is received. Each current response is peak shaped and the first and the last current values may be analyzed using multivariate data analysis. By providing a stepwise voltage sweep, the plurality of current responses generated may provide reliable information regarding the concentration of DBA present in the substance.

According to one embodiment, the step of cleaning a surface of the first electrode may comprise rotating a cleaning unit in contact with the first electrode.

A cleaning unit may be rotated in contact with the first electrode, providing a continuous cleaning of the electrode. Coatings formed on the surface of the electrode may thereby be continuously removed. The cleaning of the electrode may be by brushing, grinding, scraping or the like, of the electrode. The first electrode may be ring shaped for providing extended contact with the substance. A ring shaped first electrode may further provide continuous contact with the rotating cleaning unit.

According to one embodiment the cleaning unit may be rotated in contact with a surface of the first electrode at a speed of approximately 2 to approximately 40 rpm.

By rotating the cleaning unit in contact with a surface of the first electrode at a speed of about 2 to about 40 rpm, any coating on the surface of the first electrode is continuously removed, and continuous measurement may be performed in a reliable way. The cleaning unit may not interfere with the sending of voltage pulses. In an embodiment, the cleaning unit may be rotated at a speed of about 15 rpm. The rotating speed of the cleaning unit may vary over time, providing speed intervals for the cleaning unit.

According to one embodiment, the substance may be an absorption liquid utilized in a wet scrubber cleaning process for process gas.

In a gas cleaning process such as in a wet scrubber of a WFGD system operable to clean process gases, an absorption liquid, for example a limestone based absorption liquid, may be provided to react with acid gases in the process gas. Such acid gases may comprise sulphur dioxide. In an embodiment, the absorption liquid also includes a concentration of dibasic acid. Dibasic acid (DBA) is an aliphatic dibasic acid product containing primarily glutaric, succinic and adipic acids available commercially from companies such as INVISTA, a wholly owned subsidiary of Koch Industries, Inc., Wichita, Kans., USA and Sigma-Aldrich Corporation, St. Louis, Mo., USA. DBA is a substance used within WFGD systems to improve sulphur dioxide removal efficiency. Because DBA use increases the efficiency of sulphur dioxide removal from process gases, DBA use may be desirable. Unfortunately, use of DBA in WFGD systems is also relatively expensive. Further, overages or overdosing of DBA in the absorption liquid may lead to waste water treatment difficulties and expenses associated therewith. Accordingly, in order to minimize WFGD system operating expenses and avoid waste water treatment difficulties with its associated expenses, DBA concentration maintained to a level just sufficient to achieve a desired WFGD system efficiency without overdosing thereof, may be desirable.

According to a further aspect, there is provided a DBA sensor for measuring the concentration of DBA present in a substance in a gas cleaning device, wherein the DBA sensor includes a first electrode and a second electrode in contact with the substance, a control unit adapted to send voltage pulses through the substance by the first electrode and the second electrode, and an analyzing unit operable to receive and analyze current responses generated by the voltage pulses, wherein the analyzing unit is operable to perform multivariate data analysis.

In an embodiment of the DBA sensor, continuous measurement of DBA concentration present in a substance may be performed to obtain measurement information. The measurement information may then be used for controlling supply of DBA to the gas cleaning process. The DBA concentration present in the substance may be continuously measured even when the DBA concentration is relatively very low. Voltage pulses may be sent by the control unit through the first electrode into the substance. The current responses generated by the voltage pulses may be received through a second electrode. The second electrode may be a piece of metal. By using multivariate data analysis in the associated analyzing unit, mathematical models from samples with known DBA concentrations may be used for creating a prediction model for use to determine the DBA concentration present in the substance.

According to one embodiment, the control unit is operable to send voltage pulses in a series, such that a voltage level may be increased and/or decreased stepwise with each voltage pulse. As an alternative, the control unit may be operable to send alternating voltage pulses to produce results. As another alternative, the control unit may be operable to send average constant voltage pulses to produce results.

By increasing and/or decreasing the voltage level stepwise, a series of voltage pulses sent through the first electrode produce results with a staircase shape. The voltage pulses generating the current responses occur when the control unit increases or decreases the voltage level to a new level. The DBA sensor may also be operative to sweep the voltage level in steps from a first voltage level to a final voltage level for measurement of the DBA concentration. The first voltage level may be a negative voltage and the final voltage level may be a positive voltage, resulting in an anodic sweep. Alternatively, the first voltage level may be positive and the final voltage level may be negative, resulting in a cathodic sweep.

According to one embodiment, the analyzing unit may be operative to perform a multivariate data analysis based on peaks of the current responses generated.

Figure 4A:
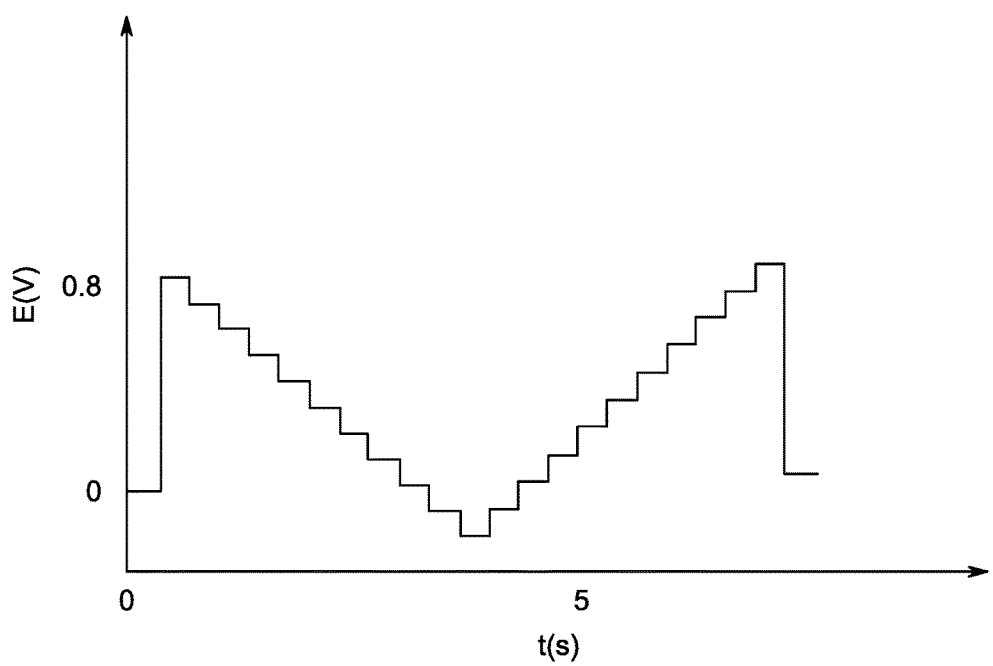
FIG. 4A is a graph of voltage level over time from a method according to an embodiment.
Figure 4B:
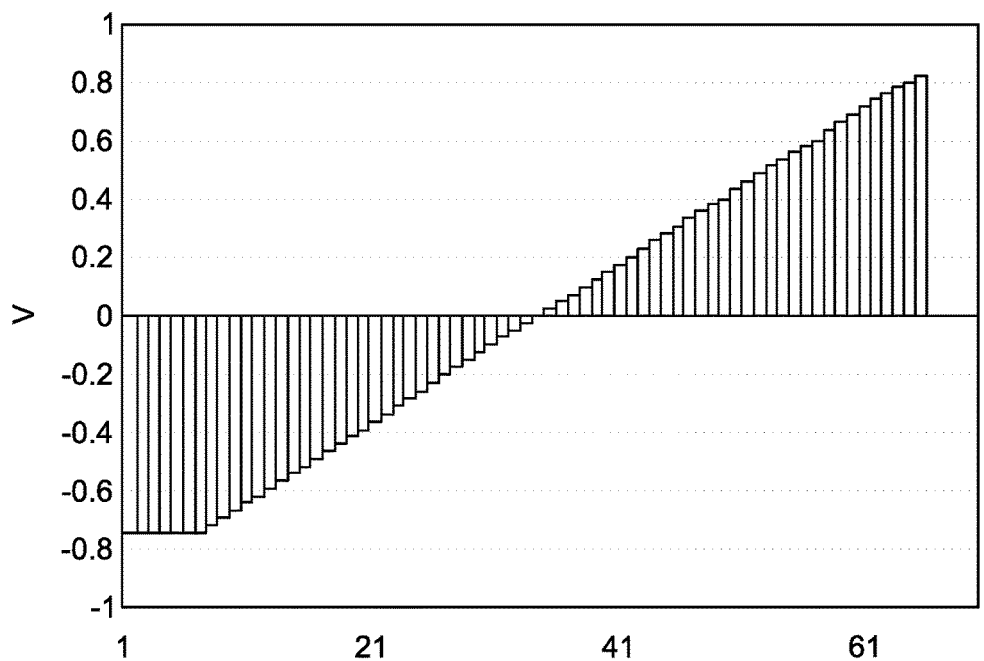
FIG. 4B is a simulation plot of voltage level pulses from a method according to an embodiment.
Figure 4C:
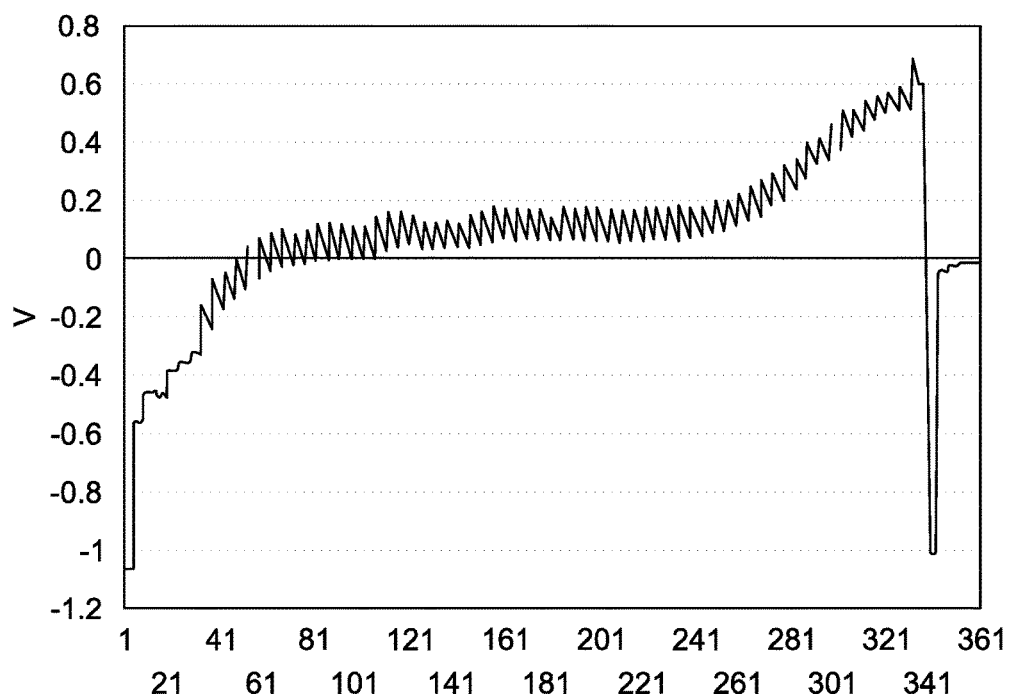
FIG. 4C is a simulation plot of a voltage corresponding to a current response generated by the voltage pulses in FIG. 4B.

A peak of the current response may provide information regarding the DBA concentration present in the substance. The current response may include a peak level and a decay of the current towards zero. If the analyzing unit analyzes the peak of the current response, a measurement of the DBA concentration is obtained. DBA may have a redox potential at which a current response may be increased compared to other potentials. If voltage pulses sent by the control unit correspond to the redox potential of DBA, the current response peak may provide an increased current level. When measuring in crude and complex media, such as liquid from a gas cleaning process, however, no clear peaked current levels at the redox potential may be obtained. This is due to interfering, more or less redox active substances in the measuring media resulting in a very complex current response. This makes the current response from a measurement very difficult to interpret. Thus, to interpret data from a current spectrum, multivariate data analysis are used. Training sets of current spectra with known DBA concentrations are then used to make mathematical prediction functions for samples with unknown DBA concentration. An example of a current spectrum is shown in FIG. 4C.

According to one embodiment, a method of controlling a wet scrubber of a WFGD system cleaning a process gas containing sulphur dioxide is provided. This method of controlling a wet scrubber of a WFGD system comprises contacting the process gas with an absorption liquid including a concentration of dibasic acid therein in an absorption vessel to absorb sulphur dioxide from the process gas, measuring the concentration of dibasic acid in the absorption liquid, and controlling, based on the measured concentration of dibasic acid, at least one wet scrubber operating parameter influencing the concentration of dibasic acid in the absorption liquid. Further according to this method, the measured concentration of dibasic acid is compared to a set point therefore. When the measured concentration of DBA present in the absorption liquid exceeds the set point, the supply of dibasic acid absorption enhancing additive to the absorption liquid is decreased. When the measured concentration of DBA present in the absorption liquid is at or near the set point, the supply of dibasic acid absorption enhancing additive to the absorption liquid is maintained. When the measured concentration of DBA present in the absorption liquid is below the set point, the supply of dibasic acid absorption enhancing additive to the absorption liquid is increased. The concentration of DBA in the absorption liquid ranges from approximately 100 to approximately 500 ppm. Continuous measurement of the DBA concentration present in the absorption liquid is desirable as DBA may be degenerated in the absorber liquid due to heat, bacteria, oxidation air, and similar conditions. This method is useful in a wet scrubber of a WFGD system used for cleaning a process gas containing sulphur dioxide. As such, the wet scrubber comprises an absorption vessel for contacting process gas with an absorption liquid that includes a concentration of dibasic acid to absorb sulphur dioxide from the process gas, a dibasic acid sensor for continuously measuring the concentration of dibasic acid in the absorption liquid, and a control unit to receive a measurement signal from the dibasic acid sensor and to control, based on the measured concentration of dibasic acid, at least one wet scrubber operating parameter influencing the concentration of dibasic acid in the absorption liquid, such as the supply of dibasic acid to the absorption liquid.

According to one embodiment, the DBA sensor may further comprise a cleaning unit operative to clean the first electrode. The first electrode may be made of platinum. When using the DBA sensor for continuously measuring, the first electrode may rather quickly become unusable due to binding onto a platinum surface of the electrode. This may form a coating on the first electrode surface and negatively affect measurement results. By providing the DBA sensor with a cleaning unit, any coating on the surface of the electrode may be removed, to ensure the reliability of the sensor. The cleaning unit may be operative to clean the first electrode in a continuous or semi-continuous manner during the continuous measurement of DBA concentration present in the substance. The cleaning unit may be a brush, a grinder, a scraper or the like.

Figure 2:
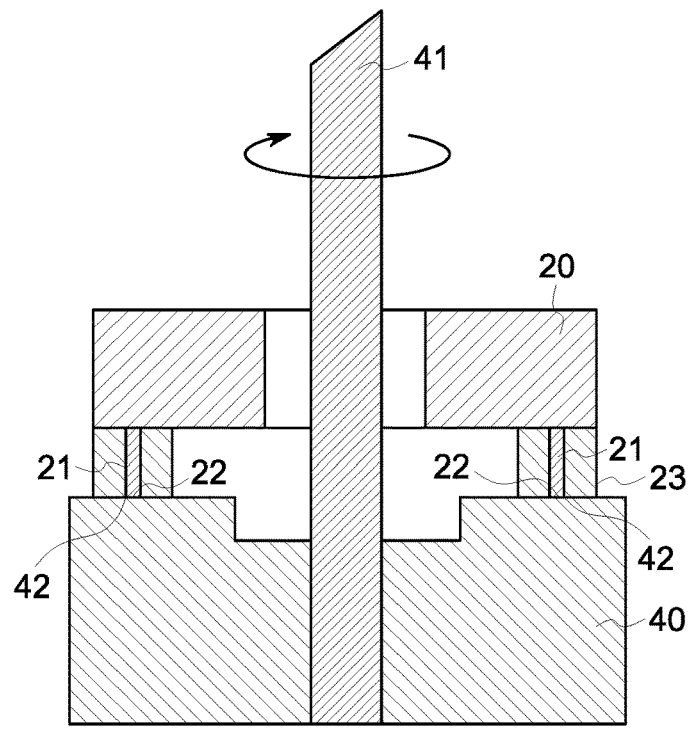
FIG. 2 is a schematic cross-sectional side view of a dibasic acid sensor.

Turning now to the figures, a dibasic acid (DBA) sensor 10 according to an embodiment of the present invention is illustrated in a perspective view in FIG. 1 and in a schematic cross-sectional side view in FIG. 2. The DBA sensor 10 comprises a base section 14, and a cover 12 that forms sides of an open space 13 for DBA detection. A sensor head 20 is located in the space 13. The sensor head 20 is formed as a tube extending into the space 13. At an axial end portion 23 of the sensor head 20, a first electrode 21 in the form of a platinum ring is provided. A surface 22 of the first electrode 21 is level with the axial end portion 23 of the sensor head 20. Although a platinum ring is provided for first electrode 21, other materials may be used such as gold, iridium, silver, and like metals.

A shaft 41 extends through interior 20*a* of the tube shaped sensor head 20. The shaft 41 is rotated by an electric motor (not shown). The shaft 41 is coupled to a grinding unit 40. The grinding unit 40 has a surface 42, which is best shown in FIG. 2, abutting the surface 22 of the first electrode 21. The shaft 41 rotates the grinding unit 40 such that the surface 42 of the grinding unit 40 grinds/cleans the surface 22 of the first electrode 21. The grinding unit 40 rotates in contact with the surface 22 of the first electrode 21 at a speed of approximately 2 to approximately 40 rpm; in one embodiment, the grinding unit rotates at a speed of approximately 15 rpm. In an embodiment, the grinding unit 40 is made of a ceramic material based on, e.g., silicon carbide or silicon nitride.

The DBA sensor 10 further comprises a second electrode 30. In an embodiment, the second electrode 30 is constructed of a metal, such as steel or the like. The second electrode 30 is arranged a distance from the first electrode 21. In the illustrated embodiment, the second electrode 30 is constituted by the metal cover 12.

A control unit 50 is arranged in the DBA sensor 10 or connected to the DBA sensor 10 and operative to send voltage pulses through the substance occupying the space between the first electrode 21 and the second electrode 30. When the DBA sensor 10 is submerged into a substance, the voltage pulses enter the substance via the first electrode 21. The second electrode 30 is adapted to receive current responses generated by the voltage pulses and pass the current responses back to the control unit 50. The control unit 50 receives and analyzes using an analyzing unit 60 the current responses generated and calculates a concentration of DBA present in the substance using a multivariate data analysis. By using multivariate data analysis in the analyzing unit 60, mathematical models from samples with known DBA concentrations are used to create a prediction model for determining the DBA concentration present in the substance.

Data from voltammetric measurements are often difficult to interpret. Each measurement consists of a number of variables. Multivariate data analysing methods, such as principal component analysis (PCA) and projection to latent structure (PLS), as is known from, for example: Wold, S., Esbensen, K. and Geladi, P. "Principal component analysis: A tutorial." Chemometrics and Intelligent Laboratory Systems 2, 37-52, 1987; and from: S. Wold, M. Sjöström and L. Eriksson" PLS-regression: a basic tool of chemometrics" Chemometrics and Intelligent Laboratory Systems, 58 (2001) 109-130, have shown to be useful in such cases. PCA is a mathematical tool, which describes the variance in experimental data. Using the PCA mathematical tool, a vector is calculated describing the direction of the largest variance in experimental data, i.e., the direction that describes the largest differences between observations. This calculated vector is called the first principal component. The second principal component is orthogonal to and thus independent of the first principal component. Further principal components can be calculated in a similar way, until most of the observations are explained. A new matrix, as defined by the principal components is then formed, and the data set is considerably reduced, depending on the significance of the different principal components, but in many cases only to two dimensions. The loading vectors describe the direction of the principal components in relation to the original variables, and the score vectors, describe the direction of the principal components in relation to the observations. Thus, a score plot can be made, showing the relationships between the original samples and how much the samples influence the system. Thus, a score plot shows the relationships between the experiments, and groupings of experiments can be used for classification.

PLS is used to make models from calibration sets of data. It is a linear method, in which PCA is performed on both the X-data (the voltammogram) and the Y-data (the concentrations). Then a linear regression is performed on each principal component between the datasets and the Y-data, giving a regression model. This regression model can be used to predict values from the voltammograms.

Further information regarding multivariate data analysis may be found in I. T. Jolliffe "Principle Component Analysis" Springer-Verlag, New York Inc. (1986) ISBN 0-387-96269-7, or K. R. Beebe, R. J. Pell and M. B. Seasholtz "Chemometrics—A practical guide" John Wiley & Sons Inc. (1998) ISBN 0-471-12451-6.

In one embodiment, the DBA sensor 10 further comprises a sensor 70 for measuring the concentration of at least one other component present in the substance.

Figure 3:
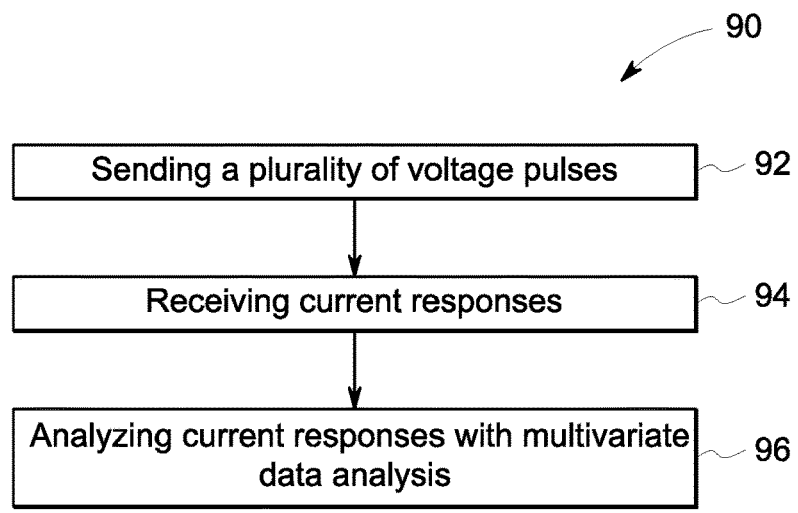
FIG. 3 is a flow chart of a method of measuring dibasic acid in a substance.

FIG. 3 is a flow chart of a method 90 for measuring a concentration of DBA present in a substance. The substance may be provided in a gas cleaning process. In a step 92, a plurality of voltage pulses is sent through the first electrode 21. The first electrode 21 is in contact with the substance. Voltage pulses are sent from the control unit 50 by the first electrode 21 and the second electrode 30 through the substance as a stepwise increasing or decreasing voltage level as shown in FIG. 4B. A staircase pattern of the voltage level sent through the first electrode 21 is formed. In an embodiment, each step involves increasing or decreasing the voltage level by about 0.05 V. In an example of the subject method, the voltage level sent through the substance as voltage pulses is, in a stepwise manner, increased from a voltage level of approximately −1.0 V to a voltage level of approximately 1.0 V in steps of approximately 0.05 V. In a further example, illustrated in FIG. 4A, the voltage level is first decreased from approximately 0.8 V down to approximately −0.1 V, in steps of approximately 0.05 V, and is then increased from approximately −0.1 V up to approximately 0.8 V, in steps of approximately 0.05 V.

In a step 94, current responses generated by the voltage pulses sent by the first electrode 21 to the second electrode 30 are received. The current responses are received by the second electrode 30. The second electrode 30 is also in contact with the substance. Each step of increasing or decreasing the voltage level generates a new current response in the second electrode 30.

In a final step 96, the current responses are analyzed using a multivariate data analysis. The concentration of DBA present in the substance may thereby be measured based on the current responses. According to one embodiment, all of the plurality of current responses is used for the measurement of DBA concentration in the substance. In one embodiment, the current response is analyzed after each sent voltage pulse. Alternatively, a series of voltage pulses are sent, generating a series of current responses, before multivariate data analysis is performed on the series of current responses.

FIG. 4B further shows an example simulation of voltage pulses in a staircase pattern. The voltage level varies over time from approximately −0.75 V to approximately 0.8 V. The values on the x axis represent number of voltage pulses. FIG. 4C shows corresponding current responses as an outgoing voltage from an electronic circuit. Information from the current responses is used for estimating the DBA concentration present in the substance, using multivariate data analysis. Each voltage pulse as shown in FIG. 4B corresponds to five measured voltage values in FIG. 4C. Hence, in the example shown in FIG. 4B and FIG. 4C, the response of each voltage pulse is measured five times during each voltage pulse. The values on the x axis of FIG. 4C represent the number of measurements.

Figure 5:
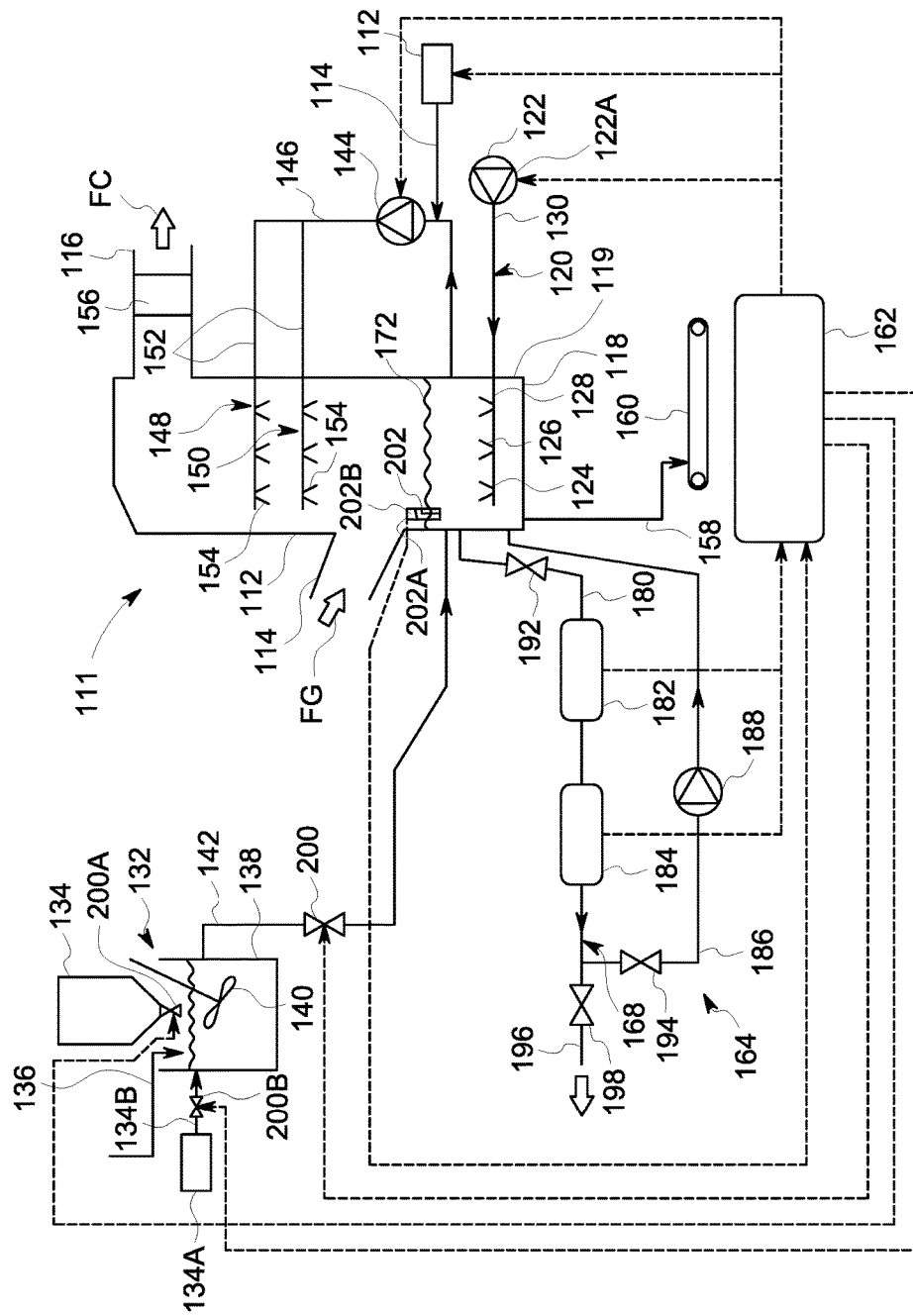
FIG. 5 is a schematic side cross sectional view of a wet scrubber comprising a dibasic acid sensor.

As an example of an application for a DBA sensor 10 according to the present disclosure, FIG. 5 illustrates a wet scrubber 111. The wet scrubber 111 is operative for removing at least a portion of the sulphur dioxide content of a process gas, in the form of a flue gas, FG, generated in a boiler (not shown) which is operative for combusting a fuel, such as coal, oil, peat, natural gas, or waste material.

The wet scrubber 111 comprises an absorption vessel in the form of a vertical open tower 112, an inlet 114 for the process gas or flue gas, FG, to be cleaned, and an outlet 116 for cleaned flue gas, FC, from which at least a portion of the sulphur dioxide content has been removed.

An absorption liquid oxidation vessel in the form of an absorption liquid tank 118 is arranged at the bottom 119 of the vertical open tower 112. The absorption liquid tank 118 fulfils the dual purposes of being a recirculation tank for absorption liquid containing a concentration of DBA, and of being a vessel in which oxidation may occur. For the latter reason, the absorption liquid tank 118 is provided with an oxidation arrangement 120. The oxidation arrangement 120 comprises an oxygen gas supply device 122 in the form a blower 122a, an oxygen distributor 124 comprising a number of nozzles 126 arranged on a distributing pipe 128, and a supply pipe 130 being fluidly connected to the blower 122 and to the distributing pipe 128 for supplying compressed oxygen containing gas, such as air, to the distributing pipe 128 and further to the nozzles 126. The nozzles 126 are arranged for distributing the air in a limestone absorption liquid including a concentration of DBA contained in the absorption liquid tank 128 to cause oxidation of sulphite contained in the limestone absorption liquid, as will be described in more detail hereinafter. It will be appreciated that the oxygen supply device 122 could, as alternative to a blower 122a, be a compressor or some other device suitable for forcing a gas containing oxygen into the absorption liquid in the absorption liquid tank 118. Furthermore, the oxygen containing gas blown by the blower 122a may, for example, be air, or rather pure oxygen gas, such as a gas comprising 90-99% by volume of oxygen, or a mixture of oxygen gas and air.

Absorbent material in the form of, for example, fresh limestone, $CaCO_3$, is supplied to the absorption liquid tank 118 from an absorbent supply system 132. The absorbent supply system 132 comprises a limestone silo 134, a water supply pipe 136, and a mixing tank 138 comprising an agitator 140. In the mixing tank 138, water is supplied via fluidly connected supply pipe 136 for mixing with limestone powder supplied from limestone silo 134 to form a limestone slurry. The limestone slurry is supplied DBA from a DBA source 134a via supply pipe 134b. The limestone slurry and DBA is supplied from the mixing tank 138 to the absorption liquid tank 118 via a fluidly connected limestone supply pipe 142. It will be appreciated that absorption liquid tank 118 may, as an alternative, be positioned outside of tower 112, and that the supply of limestone and the supply of DBA each could, as an alternative, enter the system at other locations, as a dry powder, a slurry or both. The limestone, $CaCO_3$, may be at least partly dissolved in the water:

$$CaCO_3(s)+H_2O \Leftrightarrow Ca^{2+}(aq)+CO_3^{2-}(aq) \qquad [eq. 1]$$

The wet scrubber 111 further comprises a scrubber circulation pump 144 which circulates, in absorption liquid circulation pipe 146, the limestone absorption liquid, from the absorption liquid tank 118 to two spray level systems 148, 150 positioned within open tower 112.

Each spray level system 148, 150 comprises a piping system 152 and a number of fluidly connected atomizing nozzles 154 that finely distribute limestone absorption liquid including DBA, circulated by the pump 144, to achieve effective contact between the limestone absorption liquid and the flue gas FG passing through the wet scrubber 111 and flowing substantially vertically upwards inside open tower 112. All or some of the atomizing nozzles 154 may be, for example, of the type 4CF-303120, available from Spraying Systems Co, Wheaton, Ill., USA. In the open tower 112 of the wet scrubber 111 the following reaction will occur upon absorption of sulphur dioxide, $SO_2$, comprised in the flue gas FG by the limestone absorption liquid finely distributed by the nozzles 154:

$$SO_2(g)+CO_3^{2-}(aq)+Ca^{2+}(aq) \Leftrightarrow CaSO_3(aq)+CO_2(g) \qquad [eq. 2]$$

A mist eliminator 156 is located downstream of the spray level systems 148, 150. The mist eliminator 156 removes at least a portion of the absorption liquid droplets entrained by the cleaned flue gas, FC.

In the wet scrubber 111, sulphur dioxide, $SO_2$, in the flue gas FG reacts with the limestone, $CaCO_3$, to form calcium sulphite, $CaSO_3$, which is subsequently oxidized to form gypsum, $CaSO_4$. The oxidation of calcium sulphite is performed by bubbling an oxygen containing gas, such as air, through the limestone absorption liquid that includes a concentration of DBA, using oxidation arrangement 120. The following reaction may occur in the absorption liquid tank 118:

$$CaSO_3(aq)+\tfrac{1}{2}O_2(g) \Leftrightarrow CaSO_4(s)+2H_2O \qquad [eq. 3]$$

Hence, gypsum, $CaSO_4$, sometimes described as including two water molecules, i.e., $CaSO_4 \times 2H_2O$, is formed as the end product. Hereinbefore, it has been described that the absorption of $SO_2$ generates calcium sulphite $CaSO_3$. It will be appreciated that, depending on the conditions, at least a portion of the absorbed $SO_2$ would generate calcium bisulphite, $Ca(HSO_3)_2$ (aq), which would be oxidized according to principles similar to that of [eq. 3] above.

Hence, the limestone absorption liquid comprises, in addition to the limestone and DBA, also small amounts of calcium sulphite, and as major constituent, gypsum. The gypsum formed through this process is removed from the wet scrubber 111 via a disposal pipe 158 and is forwarded to a gypsum dewatering unit, schematically indicated as belt filter 160. The dewatered gypsum may be commercially used, for example in wallboard production.

In addition to sulphur dioxide, $SO_2$, the wet scrubber 111 will remove, at least partly, also other contaminants from the flue gas. Examples of such other contaminants include sulphur trioxide, $SO_3$, hydrochloric acid, HCl, hydrofluoric acid, HF, and other acid contaminants. Still further, the wet scrubber 111 may also remove, at least partly, also other types of contaminants from the flue gas, such as for example dust particles and mercury.

A control unit 162 controls the operating parameters of wet scrubber 111. The wet scrubber 111 is provided with an absorption liquid sampling system 164, which supplies measured data to the control unit 162. The sampling system 164 comprises an absorption liquid tank sampling train 168.

The absorption liquid tank sampling train 168 comprises a pipe 180 fluidly connected to the absorption liquid tank 118. The absorption liquid collected from tank 118 by pipe 180 is forwarded, via pipe 180, to a pH analyser 182, and a sulphite analyser 184. The oxidation arrangement 120 causes an agitation of the absorption liquid contained in the tank 118, and, hence, the tank 118 may be regarded as a continuously stirred tank reactor in which the oxidation reaction occurs. Optionally, a further agitator may be arranged in the tank 118.

The pipe 180 is fluidly connected to a circulation pipe 186. A circulation pump 188 is arranged in circulation pipe 186 for pumping absorption liquid, having passed through absorption liquid tank sampling train 168, back to absorption liquid tank 118. Shut-off valves 192, 194 arranged in the pipes 180 and 186, respectively, makes it possible to collect an absorption liquid sample, via sampling pipe 196 and associated shut off valve 198, for manual analysis of the sulphite concentration and/or the pH of absorption liquid collected via absorption liquid tank sampling train 168.

Control unit 162 receives measurement signals from analysers 182 and 184, and controls, based on such measurement signals, at least one of: a control valve 200a arranged in limestone silo 134 and controlling the amount of limestone supplied to the mixing tank 138, a control valve 200b arranged in supply pipe 134b and controlling the amount of DBA supplied from DBA source 134a to the mixing tank 138, a control valve 200 arranged in limestone supply pipe 142 and controlling the amount of limestone slurry supplied from the mixing tank 138 to the absorption liquid tank 118, the scrubber circulation pump 144, and the blower 122 of the oxidation arrangement 120. Furthermore, the control unit 162 also receives measurement signals from a DBA sensor 202 including a control unit 202a and an analysing unit 202b for measuring the concentration of DBA present in the absorption liquid of the wet scrubber 111.

According to one embodiment, a method of controlling a wet scrubber 111 cleaning a process gas containing sulphur dioxide is provided. This method of controlling a wet scrubber 111 comprises contacting the process gas with an absorption liquid including a concentration of DBA therein in an open tower 112 to absorb sulphur dioxide from the process gas, measuring the concentration of DBA in the absorption liquid, and controlling, based on the measured concentration of DBA, at least one wet scrubber 111 operating parameter influencing the concentration of DBA in the absorption liquid, such as the supply of DBA to mixing tank 138. Further according to this method, the measured concentration of DBA is compared to a set point therefor. When the measured concentration of DBA present in the absorption liquid exceeds the set point, the supply of DBA absorption enhancing additive to the absorption liquid is decreased. When the measured concentration of DBA present in the absorption liquid is at or near the set point, the supply of DBA absorption enhancing additive to the absorption liquid is maintained. When the measured concentration of DBA present in the absorption liquid is below the set point, the supply of DBA absorption enhancing additive to the absorption liquid is increased. The concentration of DBA in the absorption liquid ranges from approximately 100 to approximately 500 ppm. Continuous measurement of the DBA concentration present in the absorption liquid is desirable as DBA may degenerate in the absorber liquid due to heat, bacteria, oxidation air, and similar conditions. This method is useful in a wet scrubber 11 used for cleaning a process gas containing sulphur dioxide. As such, the wet scrubber 111 comprises an open tower 112 for contacting process gas with an absorption liquid that includes a concentration of DBA to absorb sulphur dioxide from the process gas, a DBA sensor 202 for continuously measuring the concentration of DBA in the absorption liquid, and a control unit 162 to receive a measurement signal from the DBA sensor 202 and to control, based on the measured concentration of DBA, at least one wet scrubber 111 operating parameter influencing the concentration of DBA in the absorption liquid, such as the supply of DBA to the absorption liquid.

In an embodiment of this method, the DBA concentration within the absorption liquid may be continuously "measured." Further, by the present method, even a relatively low concentration of DBA may be continuously measured with relatively high accuracy. Also, continuously measuring the DBA concentration present within the absorption liquid allows for DBA concentration control with relatively high accuracy. For example, if the absorption liquid contained within the wet scrubber 111 is a limestone absorption liquid, the subject method provides for continuous measurement of DBA concentration present in the absorption liquid to thereby control the concentration of DBA present within the absorbent liquid to balance wet scrubber efficiency with minimal DBA use.

For this purpose, the subject method uses a voltammetric method for measuring the DBA concentration present in the absorption liquid. This voltammetric method uses voltage pulses sent over a first electrode 21 and a second electrode 30 of a DBA sensor 10, 202 arranged in the absorption liquid. The second electrode 30 may be a large piece of metal. The second electrode 30 may have an area, which is at least 20 times larger than that of the first electrode 21. The current responses generated by the voltage pulses are then analyzed using multivariate data analysis, and mathematical models from samples with known DBA concentrations to create a prediction model useful for determining the DBA concentration present in the substance for control thereof. The subject disclosure focuses on continuously measuring DBA concentration present in the absorption liquid. However, other components present in the limestone absorption liquid contained within a wet scrubber 111, may be continuously measured and controlled such as described herein for DBA. For example, as disclosed herein for DBA, sulfides such as $S^{2-}$ used for mercury control may be continuously measured using a sulfide sensor, like that of DBA sensor 10, to measure sulfide concentration present in the absorption liquid to thereby control the concentration of sulfides present within the absorption liquid to achieve desired mercury removal efficiency. Depending on the concentration of sulfides present within the absorption liquid, the dosing rate of a sulfide additive to the absorption liquid is controlled to achieve the desired sulfide concentration and hence mercury removal efficiency. As another example, as disclosed herein for DBA, sulfites such as $SO_3^{2-}$ may be continuously measured using a sulfite sensor that measures sulfite concentration present in the absorption liquid to thereby control the concentration of sulfites present within the absorption liquid. Depending on the concentration of sulfites present within the absorption liquid, oxygenation of the absorption liquid is increased, maintained or decreased. Further, other components present in the limestone absorption liquid contained within the wet scrubber 111, may be continuously measured and controlled such as described herein for DBA.

For example, as disclosed herein for DBA, chlorides, $Cl^-$, bromides, $Br^-$, magnesium, $Mg^{2+}$, sodium, $Na^+$, nitrates, $NO_3^{2-}$, and nitrites, $NO_2^{2-}$, may be continuously measured using a a chloride sensor, a bromide sensor, a magnesium sensor, a sodium sensor, a nitrate sensor and a nitrite sensor, with each such sensor like that of DBA sensor 10, to measure the chloride, bromide, magnesium, sodium, nitrate, and nitrite concentration, respectively, present in the absorption liquid to thereby control the concentration thereof present within the absorption liquid to enable control thereof. Hence, depending on the concentration of chloride, bromide, magnesium, sodium, nitrate and/or nitrite present within the absorption liquid, an absorption liquid release or bleed from the wet scrubber 111 via disposal pipe 158 is increased, maintained or decreased to achieve the desired concentrations to control process efficiency. Still further, DBA and other components present in the limestone absorption liquid contained within a wet scrubber 111, may be continuously measured and controlled such as described herein for DBA, using a single sensor 10, 202. As such, the single sensor 10, 202 is programmed as described above for continuously measuring the concentration of a first component present in the absorption liquid, and also programmed as described above for continuously measuring the concentrations of one or more additional components present in the absorption liquid for control thereof. For example, as disclosed above for continuously measuring the concentration of DBA, a single sensor 10, 202 using a voltammetric method sends pulses over a first electrode 21 and a second electrode 30 of a multicomponent sensor 10, 202 arranged in the absorption liquid to measure the concentration of a first component present therein. The second electrode 30 may be a large piece of metal. The second electrode 30 may have an area, which is at least 20 times larger than that of the first electrode 21. The current responses generated by the voltage pulses are then analyzed using multivariate data analysis, and mathematical models from samples with known first component concentrations to create a prediction model useful for determining the first component concentration present in the absorption liquid for control thereof. Then the same multicomponent sensor 10, 202 using a voltammetric method sends pulses over the first electrode 21 and the second electrode 30 arranged in the absorption liquid to measure the concentration of a second component present therein. The current responses generated by the voltage pulses are then analyzed using multivariate data analysis, and mathematical models from samples with known second component concentrations to create a prediction model useful for determining the second component concentration present in the absorption liquid for control thereof. Once the multicomponent sensor 10, 202 is so programmed, the single multicomponent sensor 10, 202 may be used to continuously measure the concentrations of two or more components selected from the group consisting of DBA, sulfites, sulfides, chlorides, bromides, magnesium, sodium, nitrates, and nitrites, present in the absorption liquid to enable control thereof.

While the present disclosure has been described with reference to a number of embodiments, it will be understood by those skilled in the art that various changes may be made and equivalents may be substituted for elements thereof without departing from the scope thereof. In addition, many modifications may be made to adapt a particular situation or material to the teachings of the present disclosure without departing from the essential scope thereof. Therefore, it is intended that the present disclosure not be limited to the particular embodiments disclosed as the best mode contemplated for carrying out this disclosure, but that the disclosure will include all embodiments falling within the scope of the appended claims. Moreover, the use of the terms first, second, etc., do not denote any order or importance, but rather the terms first, second, etc., are used to distinguish one element from another.

What is claimed is:

1. A method for measuring a concentration of dibasic acid in a substance in a gas cleaning process, the method comprising the steps of:
   sending a plurality of voltage pulses through the substance comprising dibasic acid by a first electrode and a second electrode of a dibasic acid sensor, wherein the first electrode and second electrode of the dibasic acid sensor are in contact with the substance comprising dibasic acid;
   receiving current responses generated by the plurality of voltage pulses; and
   analyzing the current responses using a multivariate data analysis for calculation of the concentration of dibasic acid in the substance.

2. The method according to claim 1, further comprising measuring a concentration of at least one other component present in the substance a method comprising:
   sending the plurality of voltage pulses through the substance comprising the at least one other component by the first electrode and the second electrode;
   receiving the current responses generated by the plurality of voltage pulses; and
   analyzing the current responses using the multivariate data analysis for calculation of the concentration of the at least one other component present in the substance.

3. The method according to claim 2, wherein the at least one other component in the substance is selected from the group consisting of sulfides, sulfites, chlorides, bromides, magnesium, sodium, nitrates, and nitrites.

4. The method according to claim 2, wherein the at least one other component in the substance is sulfites and chlorides.

5. The method according to claim 1, wherein the step of sending a plurality of voltage pulses comprises sending the plurality of voltage pulses in a series, stepwise by at least one of increasing or decreasing the voltage level.

6. The method according to claim 1, wherein the step of analyzing the current responses comprises analyzing peaks of the current responses using multivariate data analysis.

7. The method according to claim 1, wherein the amount of each voltage pulse sent through the substance is 0.02-1.0 V higher or lower than an immediately preceding voltage pulse.

8. The method according to claim 1, wherein analyzing the current responses using the multivariate data analysis analyzes at least two separate values of each current response for calculation of the concentration of dibasic acid in the substance based on the at least two separate values of each of the current responses.

9. The method according to claim 1, wherein analyzing the current responses using the multivariate data analysis analyzes at least two separate values comprising analyzing a peak value and at least one more value of each current response for calculation of the concentration of dibasic acid in the substance based on the at least two separate values of each of the current responses.

10. A dibasic acid sensor for measuring the concentration of dibasic acid in a substance in a gas cleaning device, wherein the dibasic acid sensor comprises:

a first electrode of the dibasic acid sensor arranged in contact with the substance comprising dibasic acid;

a second electrode of the dibasic acid sensor arranged in contact with the substance comprising dibasic acid;

a control unit operative to send voltage pulses through the substance by the first electrode and the second electrode; and an analyzing unit configured to receive and analyze current responses generated by the voltage pulses, wherein the analyzing unit is configured to perform a multivariate data analysis to calculate the concentration of dibasic acid in the substance to control the dibasic acid concentration in the gas cleaning device substance.

11. The dibasic acid sensor of claim 10, wherein the analyzing unit configured to perform a multivariate data analysis analyzes at least two separate values of each current response to calculate the concentration of dibasic acid in the substance based on the at least two separate values of each of the current responses, to control the dibasic acid concentration in the gas cleaning device substance.

12. The dibasic acid sensor according to claim 10, wherein the control unit is configured to send the voltage pulses in a series, stepwise by at least one of increased or decreased voltage level with each voltage pulse.

13. The dibasic acid sensor according to claim 10, wherein the analyzing unit is configured to perform the multivariate data analysis based on peaks of the current responses.

14. The dibasic acid sensor of claim 10, wherein the analyzing unit configured to perform a multivariate data analysis analyzes at least two separate values comprising analyzing a peak value and at least one more value of each current response to calculate the concentration of dibasic acid in the substance based on the at least two separate values of each of the current responses, to control the dibasic acid concentration in the gas cleaning device substance.

15. The dibasic acid sensor of claim 10, wherein the control unit is configured to send the voltage pulses through the substance by the first electrode and the second electrode with the analyzing unit configured to receive and analyze the current responses generated by the voltage pulses, and the analyzing unit configured to perform the multivariate data analysis to calculate a concentration of at least one other component in the substance.

16. The dibasic acid sensor according to claim 15, wherein the at least one other component is selected from the group consisting of sulfides, sulfites, chlorides, bromides, magnesium, sodium, nitrates, and nitrites.

17. The dibasic acid sensor according to claim 15, wherein the at least one other component is sulfites and chlorides.

18. A wet scrubber for cleaning a process gas containing sulphur dioxide, the wet scrubber comprising an absorption liquid including a concentration of dibasic acid to contact and absorb sulphur dioxide from the process gas, wherein the wet scrubber further comprises:

a dibasic acid sensor configured to measure the concentration of dibasic acid in the absorption liquid; and a control unit configured to receive a measurement signal from the dibasic acid sensor and to control, based on the measured concentration of dibasic acid, at least one wet scrubber operating parameter influencing the concentration of dibasic acid in the absorption liquid.

19. The wet scrubber of claim 18, wherein the dibasic acid sensor is a multicomponent sensor configured to measure the concentration of the dibasic acid and a concentration of at least one other component present in the absorption liquid, and the control unit is configured to receive the measurement signal from the multicomponent sensor and to control, based on the measured concentrations of dibasic acid and the at least one other component, at least one of the at least one wet scrubber operating parameter influencing the concentration of dibasic acid and/or the at least one other component in the absorption liquid.

* * * * *